United States Patent [19]

Cordier

[11] Patent Number: 4,540,834

[45] Date of Patent: Sep. 10, 1985

[54] PROCESS FOR THE PREPARATION OF METACHLOROPHENOLS

[75] Inventor: Georges Cordier, Francheville, France

[73] Assignee: Rhone-Poulenc Specialites Chimiques, Courbevoie, France

[21] Appl. No.: 585,503

[22] Filed: Mar. 2, 1984

[30] Foreign Application Priority Data

Mar. 2, 1983 [FR] France ............................. 83 03648

[51] Int. Cl.$^3$ ............................................. C07C 39/27
[52] U.S. Cl. ..................................................... 568/774
[58] Field of Search ......................................... 568/774

[56] References Cited

U.S. PATENT DOCUMENTS

| | | | |
|---|---|---|---|
| 3,912,782 | 10/1975 | Wedemeyer et al. | 568/774 |
| 3,912,783 | 10/1975 | Wedemeyer et al. | 568/774 |
| 4,060,562 | 11/1977 | Wedemeyer et al. | 568/774 |
| 4,410,737 | 10/1983 | Cordier | 568/774 |
| 4,410,738 | 10/1983 | Cordier | 568/774 |
| 4,410,739 | 10/1983 | Cordier | 568/774 |

FOREIGN PATENT DOCUMENTS

| | | | |
|---|---|---|---|
| 0055196 | 6/1982 | European Pat. Off. | 568/774 |
| 0055197 | 6/1982 | European Pat. Off. | 568/774 |
| 0055198 | 6/1982 | European Pat. Off. | 568/774 |

OTHER PUBLICATIONS

Tashiro et al., "Chemical Abstracts", vol. 86, p. 43346k, (1977).
Kaemmerer et al., "Chemical Abstracts", vol. 86, pp. 155, 305c, (1977).

*Primary Examiner*—Werren B. Lone
*Attorney, Agent, or Firm*—Burns, Doane, Swecker & Mathis

[57] ABSTRACT

The invention relates to a process for the preparation of metachlorophenols.

The process consists in selectively hydrodechlorinating, under the action of heat and in the liquid phase, polychlorophenols containing at least one chlorine atom in the meta position relative to the phenolic hydroxyl, by reacting these polychlorophenols with hydriodic acid in a quantity which is sufficient in relation to the chlorine atoms to be removed.

The metachlorophenols obtained are organic synthesis intermediates.

25 Claims, No Drawings

PROCESS FOR THE PREPARATION OF METACHLOROPHENOLS

The present invention relates to a process for the preparation of phenols containing a chlorine atom in at least one of the meta positions relative to the phenolic hydroxyl, by the dechlorination of more highly chlorine-substituted phenols.

For convenience, phenols containing a chlorine atom in at least one of the meta positions will hereafter be designated by the term "metachlorophenols".

Metachlorophenols, and in particular 3-chlorophenol and 3,5-dichlorophenol, are compounds of great industrial value as organic synthesis intermediates.

Various methods for the preparation of metachlorophenols have been proposed. They include especially:

methods which generate the phenolic group on chlorine-substituted aromatic compounds, such as, for example, the alkaline hydrolysis of polychlorobenzenes;

methods for the chlorination of phenols; and methods for the dechlorination of polychlorophenols.

These last methods are of very particular value in industry because of the availability of polychlorophenols, some of which are common products while others are by-products of limited value, which it is important to utilise.

Thus, for example, isomeric trichlorophenols and tetrachlorophenols, some of which contain one or two chlorine atoms in the meta position relative to the phenolic hydroxyl, are obtained in the preparation of 2,3,4,6-tetrachlorophenol and pentachlorophenol by the chlorination of 2,6-dichlorophenol, which is a by-product of the preparation of 2,4-dichlorophenol. These various polychlorophenols constitute preferred starting materials for the preparation of metachlorophenols by dechlorination. One method of removing the excess chlorine atoms consists in hydrogenating the polychlorophenols in the vapour phase or in the liquid phase, in the presence of a catalyst.

Some processes for the hydrodechlorination of polychlorophenols with hydrogen in the liquid phase and in the presence of a catalyst yield 3-chlorophenol or 3,5-dichlorophenol selectively.

Thus, French patent application No. 80/27,936 (published under No. 2,496,639) describes a process for the preparation of metachlorophenols by the selective dechlorination of polychlorophenols with hydrogen in an acid aqueous phase containing halide ions and in the presence of a catalyst based on a noble metal.

French patent application No. 80/27,937 (published under No. 2,496,640) relates to a process similar to the above process, in which the hydrodechlorination is carried out in an acid aqueous phase containing heavy metals belonging to groups 1b, 2b, 3a, 4a and 5a of the periodic table of the elements, and in the presence of a catalyst based on a noble metal.

Finally, French patent application No. 80/27,938 (published under No. 2,496,641) describes a process of hydrodechlorination with hydrogen in an organic liquid phase and in the presence of a Lewis acid and a catalyst based on a noble metal.

A common feature of these various selective and economically advantageous processes is the use of hydrogen in the presence of a catalyst based on a noble metal for effecting the dechlorination of polychlorophenols.

A process has now been found for the hydrodechlorination of polychlorophenols to metachlorophenols by reaction with hydriodic acid in the liquid phase, which dispenses with the need to use a catalyst and makes it possible to operate at lower temperatures than in the prior art.

More precisely, the present invention relates to a process for the selective preparation of a chlorophenol containing a chlorine atom in at least one of the meta positions relative to the phenolic hydroxyl, by the hydrodechlorination, under the action of heat, in the liquid phase, of a polychlorophenol of the general formula (I):

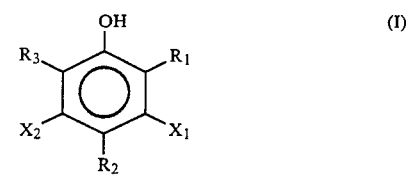

in which:

$X_1$ and $X_2$, which are identical or different, represent a chlorine atom, a hydrogen atom or an alkyl, aryl, arylalkyl, alkoxy or aryloxy radical, at least one of the symbols $X_1$ and $X_2$ representing a chlorine atom, and $R_1$, $R_2$ and $R_3$, which are identical or different, represent a chlorine atom, a hydrogen atom, an alkyl radical, an aryl or arylalkyl radical or an alkoxy or aryloxy radical, at least one of the symbols $R_1$, $R_2$ and $R_3$ representing a chlorine atom, characterised in that the said polychlorophenol is reacted with hydriodic acid in a quantity which is sufficient in relation to the chlorine atoms to be removed from the polychlorophenol (I).

More specifically, those radicals $X_1$, $X_2$, $R_1$, $R_2$ and $R_3$ which do not denote a chlorine atom represent a hydrogen atom; an alkyl radical containing from 1 to 10 carbon atoms and preferably from 1 to 4 carbon atoms, such as methyl, ethyl, n-propyl, isopropyl, n-butyl, isobutyl and t-butyl radicals; a phenyl radical; a benzyl radical; an alkoxy radical containing from 1 to 10 and preferably from 1 to 4 carbon atoms, such as methoxy, ethoxy, n-propoxy, isopropoxy and n-butoxy radicals; or the phenoxy radical.

The dechlorination reaction can be represented by the equation:

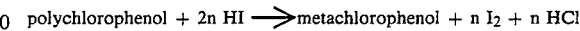

polychlorophenol + 2n HI ⟶ metachlorophenol + n I$_2$ + n HCl n representing the number (1, 2, or 3) of chlorine atoms to be removed per molecule of polychlorophenol.

The molar ratio of hydriodic acid/number of chlorine atoms to be removed from the compound (I) is generally equal to at least 2 so that the reactants are in at least stoichiometric quantities. It is quite obvious that smaller ratios can be used, but it is economically more advantageous to have a complete reaction so as to limit the problems of subsequent separation of the constituents of the final reaction mixture.

Of course, the hydriodic acid can be used either in gaseous form or in the form of a solution, especially an aqueous solution. It can also be formed in situ under the reaction conditions, for example by reacting hydrochloric acid with an alkali metal iodide.

The said molar ratio is usually between 2 and 20 and preferably between 2 and 10.

The liquid medium in which the hydrodechlorination reaction is carried out can consist of water, or of an organic solvent which is inert under the reaction conditions, especially towards the hydriodic acid and the polychlorophenol used and towards the iodine and the hydrochloric acid formed, or alternatively of a mixture of water in any proportions with an organic solvent of this type.

When they are used together with water, these organic solvents do not necessarily have to be miscible with water; their function is to dissolve the polychlorophenols used, because these compounds are only partially soluble in water.

Examples of these organic solvents which may be mentioned are aliphatic hydrocarbons such as octane and hexane; aromatic hydrocarbons such as benzene, toluene and xylenes; and chlorine-substituted aromatic hydrocarbons such as monochlorobenzene, dichlorobenzenes and trichlorobenzenes.

Of these solvents, monochlorobenzene, dichlorobenzenes and trichlorobenzenes are particularly advantageous. Even more preference is afforded to the use of dichlorobenzenes and trichlorobenzenes, essentially because of their boiling points.

If the liquid reaction medium is aqueous or partially aqueous, a proton donor, such as a strong mineral acid, is advantageously present in the medium in order to accelerate the reaction. This proton donor can be an excess of hydriodic acid relative to the stoichiometric amount, or another hydracid such as hydrochloric acid, hydrobromic acid or hydrofluoric acid, or another strong acid such as sulphuric acid or nitric acid.

If the reaction medium is only organic, it is necessary to introduce a Lewis acid in order to ensure an adequate dechlorination rate.

In acordance with the customary definition, the term "Lewis acid" denotes compounds which accept electron pairs. All types of Lewis acids can be used to put the present invention into effect, especially those mentioned in the work edited by G. A. OLAH "Friedel-Crafts and Related Reactions", 1963, volume I, pages 191 to 197. The Lewis acids which are preferably used are the acid halides, cf.: G. A. OLAH, loc. cit., pages 215 to 219, and more particularly the halides of elements of groups 3a, 4a, 5a, 1b, 2b, 4b, 5b, 6b, 7b and 8 of the periodic table of the elements (cf. Handbook of Chemistry and Physics, edited by R. C. WEAST, 53rd edition, 1972-1973), such as the chlorides, bromides, fluorides and iodides of boron, aluminium, tin, phosphorus, arsenic, bismuth, titanium, zirconium, vanadium, molybdenum, iron, cobalt, nickel, copper, zinc and cadmium. Specific examples of such halides which may be mentioned are: aluminium trichloride, aluminium tribromide, aluminium triiodide, stannic and stannous chlorides, stannic and stannous bromides, bismuth trichloride, bismuth tribromide, boron trifluoride and its complexes with electron-donating compounds such as ethers (for example boron trifluoride diethyl etherate), boron trichloride, boron tribromide, titanium, zirconium and vanadium tetrachlorides, molybdenum chlorides, ferric chloride, ferric bromide, cuprous chloride, cupric chloride and zinc chloride.

Of the abovementioned halides, it is preferred to use aluminium trichloride and tribromide.

It is quite clear that it is equally possible to use either a single Lewis acid or a mixture of several Lewis acids in carrying out the process according to the invention.

The quantity of Lewis acid, expressed as the molar ratio of Lewis acid/polychlorophenol, can vary within wide limits. Preferably, the quantity of Lewis acid is calculated so that the abovementioned molar ratio is at least 0.01 and preferably at least 0.1. There is no critical upper limit to this ratio, but, for obvious practical reasons, it should not be greater than 2 or, preferably, greater than 1.

The pressure under which the hydrodechlorination reaction is carried out is the autogenous pressure of the various reactants.

However, if the liquid medium consists of an organic solvent, the pressure increases during the reaction because hydrochloric acid is evolved. In this case, it is preferred to limit the pressure to at most 100 bars and preferably to at most 50 bars. This can be achieved by periodic degassing; in that case, it is good to compensate any losses of hydriodic acid by adding this reactant. It is also possible to circulate a stream of hydriodic acid through the reaction medium, the hydrochloric acid formed being removed continuously. During these various pressure adjustments, the pressure must not be reduced below 3 bars or, preferably, below 5 bars.

The hydrodechlorination reaction temperature is generally between 90° C. and 250° C. The reaction is slow at lower temperatures; higher temperatures have no industrial advantage.

Preferably, the temperature at which the reaction is carried out is between 110° C. and 220° C.

Examples which may be mentioned of polychlorophenols of the formula (I) which can be used as starting materials in the process according to the present invention are: 2,3-dichlorophenol, 2,5-dichlorophenol, 3,4-dichlorophenol, 2,3,4-trichlorophenol, 2,3,6-trichlorophenol, 2,3,5-trichlorophenol, 2,4,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-2-ethoxyphenol, 3,4,5-trichloro-2-ethoxyphenol, 3,4-dichloro-2-phenylphenol and 3,5,6-trichloro-2-phenylphenol.

The following may be mentioned amongst the phenols containing a chlorine atom in at least one of the meta positions relative to the phenolic hydroxyl, which can be prepared by the process according to the present invention: 3-chlorophenol, 3,5-dichlorophenol, 3-chloro-6-methylphenol, 3-chloro-5-methylphenol, 3-chloro-4-methylphenol, 3,5-dichloro-4-methylphenol, 5-chloro-3,4-dimethylphenol, 3,5-dichloro-4-ethylphenol, 3,5-dichloro-4-propylphenol, 3,5-dichloro-4-t-butylphenol, 3-chloro-2-benzylphenol, 3-chloro-2-methoxyphenol, 3-chloro-6-methoxyphenol, 3,5-dichloro-2-methoxyphenol, 3-chloro-5-methoxyphenol, 3-chloro-6-phenoxyphenol, 3,5-dichloro-6-phenoxyphenol, 3-chloro-2-ethoxyphenol and 3-chloro-2-phenylphenol.

The process according to the invention can be carried out continuously or batchwise. At the end of the reaction, the metachlorophenol or metachlorophenols can be separated from the reaction medium by any method which is in itself known, for example by solvent extraction and or by distillation.

The process according to the invention is particularly advantageous because it makes it possible to obtain metachlorophenols selectively under relatively moderate pressures and without using a catalyst.

The examples which follow illustrate the invention and show how it can be put into practice.

EXAMPLE 1

The following are introduced into a tantalum-lined autoclave having a capacity of 225 cm$^3$:
 0.08 mol of pentachlorophenol
 0.04 mol of anhydrous aluminium chloride
 40 cm$^3$ of orthodichlorobenzene.

The autoclave is closed, the air which it contains is removed by purging with nitrogen and the autoclave is then cooled. It is then connected to a cylinder containing liquefied dry hydriodic acid and 0.64 mol of HI is introduced into the reactor.

The temperature of the reactor charged in this way is raised to 135° C. under autogenous pressure and the reaction is allowed to proceed for 1 hour 30 minutes at this temperature.

The reactor is then cooled and degassed and its contents are discharged and hydrolysed with 50 cm$^3$ of an aqueous solution containing 1 mol of HCl/liter.

The organic phase containing the iodine and the polychlorophenols is separated from the aqueous phase. The iodine and the chlorophenols which the aqueous phase still contains are removed by washing with a suitable quantity of 1,2-dichlorobenzene.

The iodine is removed (and thus recovered) from the organic phase by distillation with part of the dichlorobenzene, while the less volatile polychlorophenols remain in the still.

Analysis of the contents of the still by vapour phase chromatography (VPC) indicates that the degree of conversion (DC) of the pentachlorophenol is 100%. The yield of 3,5-dichlorophenol, relative to the pentachlorophenol initially used, is 96.7%.

The following reaction intermediates also remain: 2,3,5-trichlorophenol (RY: 2.3%) and 2,3,5,6-tetrachlorophenol (RY: 1%).

EXAMPLE 2

The procedure of Example 1 is followed, but only 0.48 mol of HI is introduced.

After a reaction time of 1 hour at 135° C., it is found that the DC of the pentachlorophenol (PCP) is 94% and that the RY of 3,5-dichlorophenol (3,5-DCP) is 60%.

The following are also found:
 RY of 2,3,5,6-tetrachlorophenol (2,3,5,6-TTCP) = 19.5%
 RY of 2,3,5-trichlorophenol (2,3,5-TCP) = 13.5%.
The latter can optionally be recovered and recycled.

EXAMPLE 3

The procedure of Example 1 is followed, but 0.02 mol of AlCl$_3$ is introduced instead of 0.04 mol.

After a reaction time of 15 hours at 135° C., it is found that the degree of conversion of the PCP is 100%.

The RY of 3,5-DCP is 73.3%.
The following are also found:
 RY of unconverted 2,3,5,6-TTCP = 5%
 RY of unconverted 2,3,5-TCP = 0.7%
 RY of 3-chlorophenol (3-CP) = 19%.

EXAMPLE 4

The procedure of Example 1 is followed, but 0.008 mol of AlCl$_3$ is introduced instead of 0.04 mol.

After a reaction time of 8 hours at 150° C., it is found that the degree of conversion of the PCP is 100%.
 RY of 2,3,5,6-TTCP = 6.9%
 RY of unconverted 2,3,5-TCP = 3.5%
 RY of 3,5-DCP = 77%.
3-CP was also formed: RY = 12%.

EXAMPLE 5

The procedure of Example 1 is followed, but the PCP is replaced by 2,3,4,6-TTCP.

After a reaction time of 6 hours at 135° C., it is found that the degree of conversion of the 2,3,4,6-TTCP is 97%.
 RY of 3-CP = 77%.
The following also remain:
 2,3,6-TCP (RY = 4%)
 dichlorophenol (2,3-DCP and 2,5-DCP) (RY = 9.5%).
The following were also formed:
 phenol (RY = 4.9%)
 2-chlorophenol (RY = 1%).

EXAMPLE 6

Example 1 is repeated, 2,3,6-TCP being used as the substrate and the following being introduced:
 2,3,6-TCP: 0.08 mol
 HI: 0.427 mol
 AlCl$_3$: 0.04 mol.

After a reaction time of 6 hours at 135° C., it is found that the degree of conversion of the 2,3,6-TCP is 100%.
 RY of 3-CP = 86%.
The following also remain:
 2,3-DCP (RY = 6%)
 2,6-dichlorophenol (RY = 4%).
The following was also formed:
 phenol (RY = 3.7%).

EXAMPLE 7

(aqueous medium)

The following are introduced into a tantalum-lined autoclave having a capacity of 225 cm$^3$:
 0.05 mol of 3,4-DCP
 100 cm$^3$ of an aqueous solution of HI containing 4 mol/liter.

The autoclave is closed and the air which it contains is removed by purging with nitrogen. The temperature of the autoclave is raised to 190° C. under autogenous pressure and these conditions are maintained for 2 hours.

The reaction mixture is extracted with toluene.

After removal of the iodine, analysis by VPC gives:
 DC of the 3,4-DCP = 98%
 RY of 3-CP = 85.3%
 RY of 4-CP = 12.6%.

EXAMPLES 8 TO 12

In Examples 8 to 12, the operation described in Example 7 is repeated but changes are made either in the substrate or in the quantity of HI, its concentration in water and, if appropriate, the initial concentration of protons by adding hydrochloric acid.

The results obtained are collated in the table below:

TABLE I

| Example | Substrate (mmol) | HI (mmol) | HCl (mmol) | H$_2$O (cm$^3$) | Temp. (°C.) | Duration (hours) | DC % | RY % 3-CP | RY % 4-CP | RY % 2-CP |
|---|---|---|---|---|---|---|---|---|---|---|
| 8 | 3,4-DCP 50 | 100 | 0 | 25 | 190 | 2 | 62 | 59.7 | 2.7 | 0 |
| 9 | 3,4-DCP 50 | 100 | 0 | 50 | 190 | 4 | 54 | 54 | 0 | 0 |
| 10 | 3,4-DCP 50 | 100 | 900 | 100 | 190 | 2 | 79 | 71.5 | 7.8 | 0 |
| 11 | 2,3-DCP 50 | 400 | 0 | 100 | 190 | 2 | 75 | 75 | 0 | 0 |
| 12 | 2,3-DCP 50 | 100 | 0 | 25 | 190 | 4 | 85 | 85 | 0 | 0 |

EXAMPLE 13

Example 7 is repeated, the following being introduced:
2,3,6-TCP = 25 mmol
HI = 120 mol
HCl = 840 mmol
Water = 100 cm$^3$.

After a reaction time of 16 hours at 190° C. under autogenous pressure, the results are as follows:
DC of the 2,3,6-TCP = 100%
RY of 3-CP = 72%
RY of 2,3-DCP = 10%
RY of 2-CP = 8%
RY of 2,6-DCP = 10%.

EXAMPLE 14

Example 7 is repeated, the following being introduced:
PCP = 16 mmol
HI = 160 mmol
HCl = 960 mmol
Water = 100 cm$^3$.

After a reaction time of 6 hours at 190° C. under autogenous pressure, the results are as follows:
DC of the PCP = 92%
RY of 3,5-DCP = 76.3%
RY of 2,3,5-TCP = 11.3%
RY of 2,3,5,6-TTCP = 3.1%.

EXAMPLE 15

Example 7 is repeated, the following being introduced:
PCP = 10 mmol
HI = 80 mmol
Orthodichlorobenzene = 15 cm$^3$
Water = 10 cm$^3$.

After a reaction time of 16 hours at 190° C. under autogenous pressure, the results are as follows:
DC of the PCP = 100%
RY of 3,5-DCP = 78%
RY of 2,3,5-TCP = 13.3%
RY of 2,3,5,6-TTCP = 8.7%.

I claim:

1. A process for the preparation of a meta-chlorophenol, comprising selectively hydrodechlorinating with hydriodic acid, in liquid phase, a polychlorophenol having the general formula (I):

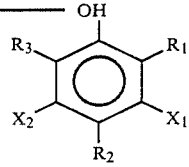

wherein
X$_1$ and X$_2$, which are identical or different, are each chloro, hydrogen, alkyl, aryl, arylakyl, alkoxy or aryloxy, with the proviso that at least one of X$_1$ and X$_2$ is chloro, and R$_1$, R$_2$, and R$_3$, which are identical or different, are each chloro, hydrogen, alkyl, aryl, arylakyl, alkoxy or aryloxy, with the proviso that at least one of R$_1$, R$_2$ and R$_3$ is chloro, said reaction being carried out in the presence of such amount of hydriodic acid as to hydrodechlorinate the desired number of chlorine atoms.

2. The process as defined by claim 1, wherein the molar ratio of hydriodic acid/number of chlorine atoms to be removed per molecule of the polychlorophenol (I) is at least 2.

3. The process as defined by claim 1, wherein the molar ratio of hydriodic acid/number of chlorine atoms to be removed per molecule of polychlorophenol (I) is in the range between 2 and 10.

4. The process as defined by claim 1, wherein those radicals X$_1$, X$_2$, R$_1$, R$_2$ and R$_3$ which do not denote chloro represent hydrogen; an alkyl radical containing from 1 to 10 carbon atoms; a phenyl radical; a benzyl radical; an alkoxy radical containing from 1 to 10 carbon atoms; or a phenoxy radical.

5. The process as defined by claim 1, wherein the reaction medium comprises water or a mixture of water and an inert organic solvent.

6. The process as defined by claim 5, wherein the reaction is carried out in the presence of a strong mineral acid.

7. The process as defined claim 5, wherein the reaction is carried out in the presence of hydrochloric acid.

8. The process as defined by claim 4, wherein the polychlorophenol (I) is dissolved in an inert organic solvent and said reaction is carried out in the presence of a Lewis Acid.

9. The process as defined by claim 8, wherein said Lewis acid used comprises a halide of elements of groups 3a, 4a, 5a, 1b, 2b, 4b, 5b, 6b, 7b and 8 of the periodic table of the elements.

10. The process as defined by claim 8, wherein said Lewis acid comprises an aluminum halide.

11. The process as defined by claim 8, wherein the quantity of said Lewis acid is such that the molar ratio of Lewis acid/polychlorophenol of the formula (I) is at least 0.01 and not more than 2.

12. The process as defined by claim 8, wherein the quantity of said Lewis acid is such that the molar ratio of Lewis acid/polychlorophenol of the formula (I) is at least 0.1 and not more than 1 and the process is conducted at a temperature between about 90° and 250° C. and at a pressure between about 3 and 100 bars.

13. The process as defined by claim 4, wherein the temperature is in the range of from about 90° C. to about 250° C.

14. The process as defined by claim 1, wherein the temperature is in the range of from about 100° C. to about 220° C.

15. The process as defined by claim 4, wherein the process is conducted at autogenous pressure not exceeding 100 bars.

16. The process as defined by claim 1, wherein the process is conducted at an autogenous pressure in the range of from about 5 to about 50 bars.

17. The process as defined by claim 1, wherein said chlorophenol is pentachlorophenol, 2,3,4,6-tetrachlorophenol, 2,3,6-trichlorophenol or 3,4-dichlorophenol.

18. A process as defined by claim 1, wherein said hydriodic acid is formed in situ under reaction conditions.

19. A process as defined by claim 1, wherein said hydriodic acid is formed in situ under reaction conditions by reacting hydrochloric acid with an alkali metal halide.

20. A process for the selective preparation of a monochlorophenol or dichlorophenol containing a chlorine atom in at least one meta position relative to the phenolic hydroxyl by hydrodechlorination of a polychlorophenol selected from the group consisting of at least one member of the group consisting of pentachlorophenol, 2,3,4,6-tetrachlorophenol, 2,3,6-trichlorophenol and 3,4-dichlorophenol,
which process comprises
mixing said polychlorophenol with dichlorobenzene and aluminum chloride, the molar ratio of aluminum chloride to polychlorophenol being at least 0.1 and not more than 2,
adding hydriodic acid to the resulting polychlorophenol solution in a molar ratio of hydriodic acid to the number of chlorine atoms to be removed per molecule of polychlorophenol of between 2 and 10,
and heating the resulting mixture at a temperature of from about 100° C. to about 200° C. and at a pressure of from about 5 to about 50 bars until the polychlorophenol is substantially converted and the desired metachlorophenol is formed,
and separating the metachlorophenol from the reaction mixture.

21. A process as defined by claim 20, wherein the ratio of aluminum chloride to polychlorophenol is not more than 1.

22. A process as defined by claim 20, wherein the hydriodic acid is added to the process is in dry gaseous form.

23. A process as defined by claim 20, wherein the hydriodic acid is added to the process as an aqueous solution.

24. A process as defined by claim 20, wherein said hydriodic acid is formed in situ under reaction conditions.

25. A process as defined by claim 20, wherein said hydriodic acid is formed in situ under reaction conditions by reacting hydrochloric acid with an alkali metal halide.

* * * * *